Jan. 24, 1967 D. L. ARMSTRONG Plant Pat. 2,705
ROSE PLANT
Filed Nov. 17, 1965
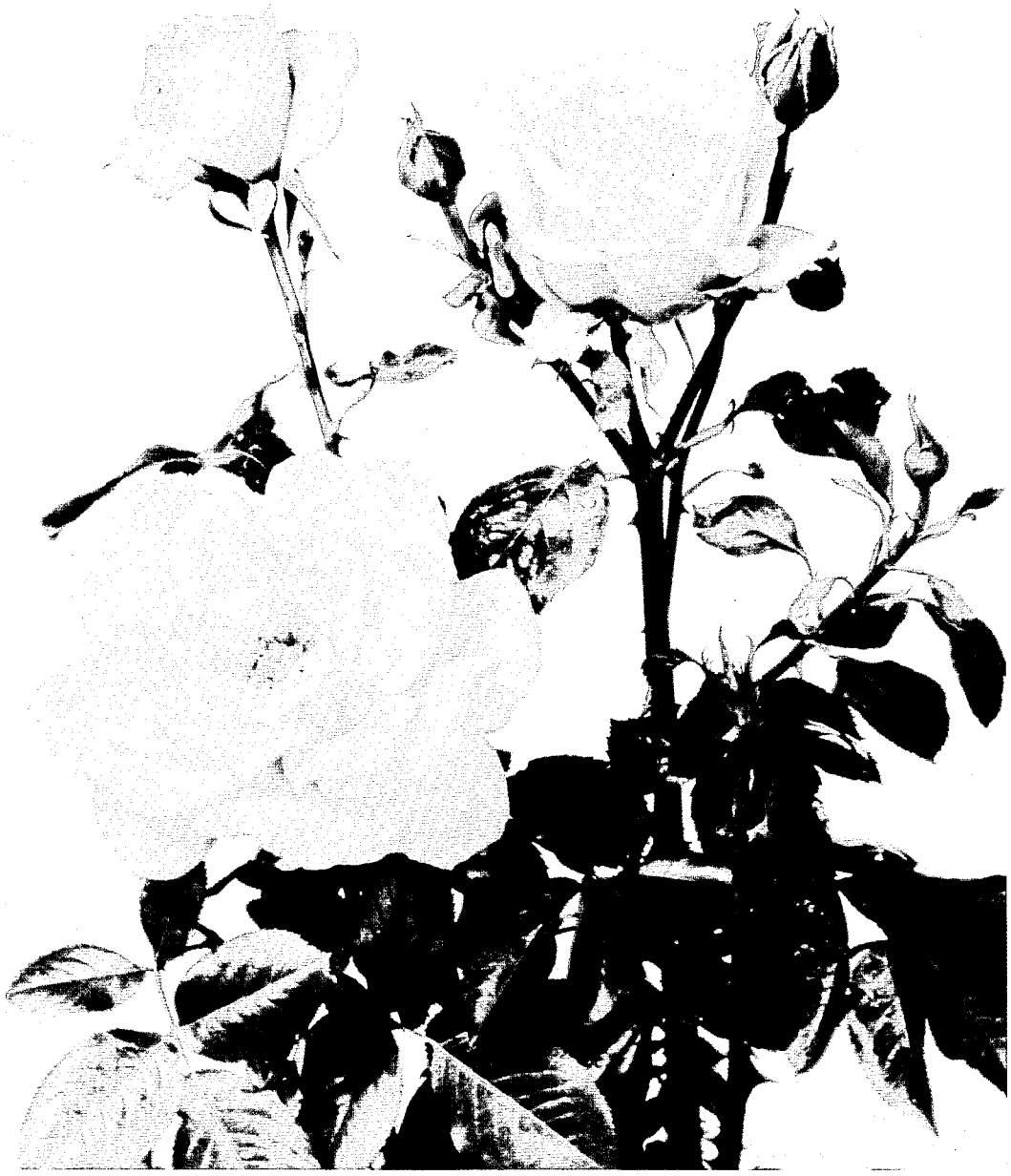
Inventor.
D. L. Armstrong
By: Robb & Robb
Attorneys.

United States Patent Office

Plant Pat. 2,705
Patented Jan. 24, 1967

2,705
ROSE PLANT

David L. Armstrong, Ontario, Calif., assignor to Armstrong Nurseries, Inc., Ontario, Calif., a corporation of California Filed Nov. 17, 1965, Ser. No. 508,401
1 Claim. (Cl. Plt.—20)

The present invention relates to a new and distinct variety of rose plant of the hybrid tea class, which was originated by me by crossing the variety known as "Roundelay" (Plant Patent No. 1,280) with the variety known as "El Capitan" (Plant Patent No. 1,796), the former being the seed parent, and the latter being the pollen parent.

The general objective of this breeding was to produce a new and improved variety of rose plant which bears red flowers, while combining the double flower petalage and the large, attractive, disease-resistant foliage characteristics of the parent variety "Roundelay" with the large flower size and good flower form of the parent variety "El Capitan," together with the great vigor and floriferousness of both parents. This objective was fully achieved, along with other desirable improvements, as evidenced by the following unique combination of characteristics which are outstanding in the new variety and which distinguish it from its parents, as well as from all other varieties of which I am aware:

(1) A very vigorous, attractive, and upright-spreading plant habit;

(2) Large, attractive, leathery, semi-glossy and disease-resistant dark green foliage;

(3) Very good floriferousness, with the flowers borne both singly and in small clusters;

(4) Medium to long flower stems;

(5) Attractive urn-shaped flower buds;

(6) Medium to large, double flowers; and (7) A distinctive and very attractive, rich and often glowing red flower color ranging between Geranium Lake and Signal Red.

In comparison with its seed parent, "Roundelay," the new variety bears flowers of somewhat larger size and the flowers have a more orange-red color instead of the dark red flower color of this parent.

As compared with its pollen parent, "El Capitan," the flowers of the new variety are orange-red in color instead of near cherry red like the flower color of this parent.

Asexual reproduction of my new variety by budding, as performed at Ontario, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated (W)) and Robert Ridgway's Color Standards and Nomenclature (hereinafter abbreviated (R)), as indicated:

Type: Tall; bush; outdoor; seedling; for cut flowers and for garden decoration.
Class: Hybrid tea.
Breeding: Seedling.
*Seed parent.*—"Roundelay."
*Pollen parent.*—"El Capitan."
Propagation: Holds its distiguishing characteristics through succeeding propagations by budding.

*Flower*

Locality where grown and observed: Ontario, California.
Flowers Borne: Sometimes singly and sometimes from 2 to 5 to stem; in irregular clusters; on strong stems of medium length.
Quantity of bloom: Abundant, outdoors.
Continuity: Nearly continuous during growing season.
Fragrance: Slight.
Bud:
*Peduncle.*—From short to average length; average caliper; erect; smooth; with few to several small stipitate glands and none to few small prickles. Color—near Mignonette, Plate XXXI (R), overlaid with near Army Brown, Plate XL (R) on side exposed to sun.
*Before calyx breaks.*—Size—medium. Form from short to medium length; ovoid.
*As calyx breaks.*—Color—between Dahlia Purple, Plate 931, page 178 (W) and Purple Madder, Plate 1028, page 181 (W).
*Sepals.*—Inner surface—with fine, wooly tomentum. Outer surface usually with several to many small stipitate glands. Alternate margins—lined with fine, wooly tomentum. Other margins—with few to several small stipitate glands and small, slender foliaceous parts.
*As first petal opens.*—Size—average. Form—from short to medium length; ovoid; usually urn-shaped. Color: Outside—near Blood Red, Plate 820/3, page 166 (W), blending with near Cardinal Red, Plate 822/1, page 168 (W) toward base of petal; inside—near Geranium Lake, Plate 20, page 20 (W), blending with near Cherry, Plate 722/1, page 157 (W) toward base of petal, with small area at base near attachment near Canary Yellow, Plate 2/1, page 2 (W).
*Opening.*—Opens up well; is not retarded or prevented from opening by cold, hot, wet or dry weather.
Bloom:
*Size (when fully open).*—From average to large; from 4 inches to 5 inches.
*Petalage.*—Double; from 25 to 35 petals plus 4 to 8 petaloids; arranged irregularly.
*Form.*—High-centered at first, but becoming cupped to high-centered; petals being at first tightly cupped, with tips reflexed outward, but later becoming loosely cupped, with tips reflexed outward, at maturity; outside and intermediate petals of newly opened flower usually reflexed slightly outward along apex and sometimes along edges; all petals of 3-days open flower usually reflexed outward along both apex and edges.
Petals:
*Texture.*—Medium thickness; moderately leathery.
*Appearance.*—Inside—velvety. Outside—satiny.
*Shape.*—Outside—between round and broadly obovate, with apex flat and usually with 1 or 2 notches. Intermediate—broadly obovate, with apex rounded and sometimes with 1 or 2 notches. Inside—obovate, but sometimes irregular, with apex rounded.

This description of a newly opened flower was made from a rose grown outdoors during the month of June at Ontario, California:

*Color.* — Outer petal: Outside surface — between Turkey Red, Plate 721/3, page 94 (W) and Currant Red, Plate 821/3, page 167 (W); inside surface—between Geranium Lake, Plate 20/1, page 20 (W) and Blood Red, Plate 820/3, page 166

(W), with small area at base of petal near attachment near Canary Yellow, Plate 2/3, page 2 (W). Intermediate petal: Outside surface—between Turkey Red, Plate 721/3, page 94 (W) and Blood Red, Plate 820/3, page 166 (W); inside surface—between Signal Red, Plate 719/2, page 93 (W) and Geranium Lake, Plate 20, page 20 (W), with small area at base of petal near attachment near Canary Yellow, Plate 2/2, page 2 (W). Inner petal: Outside surface—between Turkey Red, Plate 721/2, page 94 (W) and Blood Red, Plate 820/2, page 166 (W); inside surface—between Signal Red, Plate 719/1, page 93 (W) and Geranium Lake, Plate 20, page 20 (W), with small area at base of petal near attachment near Canary Yellow, Plate 2/2, page 2 (W).

This description was made from a rose that was open for three days outdoors during the month of June at Ontario, California:

*Color.*—Outer petal: Outside surface—between Carmine, Plate 21, page 21 (W) and Turkey Red, Plate 721/3, page 94 (W); inside surface—between Geranium Lake, Plate 20/1, page 20 (W) and Orient Red, Plate 819/3, page 165 (W). Inner petal: Outside surface—between Geranium Lake, Plate 20/1, page 20 (W) and Carmine, Plate 21, page 21 (W); inside surface—between Geranium Lake, Plate 20, page 20 (W) and Orient Red, Plate 819/2, page 165 (W).

*General color effect.*—Newly opened flower—between Geranium Lake, Plate 20, page 20 (W) and Signal Red, Plate 719/2, page 93 (W). 3-days open—between Geranium Lake, Plate 20, page 20 (W)and Orient Red, Plate 819/2, page 165 (W).

*Behavior.*—Drop off cleanly; not particularly affected by cold, hot, wet or dry weather.

*Flower longevity.*—On bush in garden—4 or 5 days in June. Cut roses grown outdoors and kept at livingroom temperatures—3 or 4 days in June.

*Reproductive organs*

Stamens: Average number; arranged regularly about pistils; a few mixed with petaloids.

Filaments: Medium length (from 6 mm. to 12 mm. long); most with anthers. Color—upper ⅔ of filament near Rose Madder, Plate 23/3, page 23 (W), with remainder near Dresden Yellow, Plate 64/2, page 64 (W).

Anthers: From small to medium size; all open approximately at once. Color: Upper side—margins near Maize Yellow, Plate 607, page 69 (W), with remainder near Straw Yellow, Plate 604/3, page 67 (W); under side—margins near Maize Yellow, Plate 607, page 69 (W), with remainder near Straw Yellow, Plate 604/3, page 67 (W).

Pollen: Abundant. Color—near Indian Yellow, Plate 6/1, page 6 (W).

Pistils: Average number (approximately 80).

Styles: Moderately even; from short to average length; very thin; bunched. Color—upper ½ of style near Crimson, Plate 22/1, page 22 (W), with remainder near Uranium Green, Plate 63/2, page 63 (W).

Stigma: Color—near Maize Yellow, Plate 607/3, page 69 (W).

Ovaries: Usually all enclosed in calyx.

Hips: Average length; globular; smooth; walls thick and fleshy. Color (half mature)—near Absinthe Green, Plate XXXI (R), overlaid with near Snuff Brown, Plate XXIX (R) on side exposed to sun.

Sepals: Falling soon; medium length; straight. Color: Inside—near Vetiver Green, Plate XLVII (R); outside near Deep Olive, Plate XL (R).

Seeds: From few to average number (from 6 to 15); from medium size to large.

*Plant*

Foliage:

*Leaves.*—Compound of usually 3 to 7 leaflets; abundant; large; leathery; semi-glossy.

*Leaflets.* — Shape — broadly oval. Apex — acute. Base—round. Margin—simply serrate.

*Color.*—Mature: Upper surface—near Cress Green, Plate XXXI (R); under surface near Light Elm Green, Plate XVII (R). Young: Upper surface—near Forest Green, Plate XVII (R); under surface—near Chromium Green, Plate XXXII (R).

*Rachis (the supporting stem of the compound leaf).*—Average size. Upper side—grooved; with several to many small stipitate glands on edges. Under side—smooth; with stipitate glands and few to several small prickles.

*Stipules.*—Medium length; narrow; with short points turning out at an angle of more than 45°.

*Disease resistance.*—Better than average resistance to mildew, as determined from comparison with other rose varieties grown under comparable cultural condition at Ontario California.

Growth:

*Habit.*—Upright—spreading; much-branched.

*Growth.*—Vigorous.

*Canes.*—From medium caliper to heavy.

*Main stems.*—Color—near Deep Grape Green, Plate XLI (R). Large prickles—many; medium length; almost straight; with long base; color—near Cinnamon, Plate XXIX (R). Small prickles—many; color—near Cinnamon, Plate XXIX (R). Hairs—none.

*Branches.*—Color—near Biscay Green, Plate XVII (R). Large prickles—many; medium length; from almost straight to hooked slightly downward; with long base; color—near Russet, Plate XV (R). Small prickles—from several to many; color—near Russet, Plate XV (R). Hairs—none.

*New shoots.*—Color—near Light Yellowish-Olive, Plate XXX (R), overlaid with near Dark Indian Red, Plate XXVII (R) on side exposed to sun. Large prickles—many; medium length; from almost straight to hooked slightly downward; with long base; color—near Deep Corinthian Red, Plate XXVII (R). Small prickles—several; color—near Deep Corinthian Red, Plate XXVII (R). Hairs—none.

A new and distinct variety of rose plant of the hybrid tea class, substantially as herein shown and described, characterized particularly as to novelty by the unique combination of a very vigorous, attractive, upright-spreading plant habit, large, attractive, leathery and semi-glossy dark green disease-resistant foliage, very good floriferousness, with the flowers borne both singly and in small clusters on medium to long flower stems, said flowers beginning as attractive urn-shaped buds which become medium to large, double flowers when open, and a distinctive and very attractive, rich and often glowing flower color ranging between Geranium Lake and Signal Red.

No references cited.

ABRAHAM G. STONE, *Primary Examiner.*

R. E. BAGWILL, *Assistant Examiner.*